United States Patent
Stadtmiller et al.

(10) Patent No.: US 7,192,274 B2
(45) Date of Patent: Mar. 20, 2007

(54) CERAMIC ORTHODONTIC APPLIANCE WITH ARCHWIRE SLOT LINER

(75) Inventors: Allen J. Stadtmiller, Arcadia, CA (US); William E. Wyllie, II, Pasadena, CA (US); Jirina V. Pospisil, Hacienda Heights, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 431 days.

(21) Appl. No.: 10/730,344

(22) Filed: Dec. 8, 2003

(65) Prior Publication Data

US 2005/0123875 A1    Jun. 9, 2005

(51) Int. Cl.
 *A61C 7/00*    (2006.01)
(52) U.S. Cl. .......................................... 433/8
(58) Field of Classification Search .................... 433/8, 433/9, 10, 11, 12, 13, 14, 15, 16, 17; 29/896.1, 29/896.11
See application file for complete search history.

(56) References Cited

U.S. PATENT DOCUMENTS

| | | | |
|---|---|---|---|
| 3,930,311 A | 1/1976 | Andrews | |
| 4,249,897 A | 2/1981 | Anderson | |
| 4,299,569 A | 11/1981 | Frantz | |
| 4,302,532 A | 11/1981 | Wallshein | |
| 4,850,865 A | 7/1989 | Napolitano | |
| 4,954,080 A | 9/1990 | Kelly et al. | |
| D315,957 S | 4/1991 | Kelly et al. | |
| 5,161,969 A | 11/1992 | Pospisil et al. | |
| 5,252,066 A | 10/1993 | Fairhurst | |
| 5,254,002 A | 10/1993 | Reher et al. | |
| 5,358,402 A | 10/1994 | Reed et al. | |
| 5,366,372 A | 11/1994 | Hansen et al. | |
| 5,380,196 A | 1/1995 | Kelly et al. | |
| 5,439,379 A * | 8/1995 | Hansen ........................... 433/8 |
| 5,470,228 A | 11/1995 | Franseen et al. | |
| 5,816,801 A * | 10/1998 | Farzin-Nia et al. ............ 433/8 |
| 6,142,775 A | 11/2000 | Hansen et al. | |
| 6,168,428 B1 * | 1/2001 | Voudouris ..................... 433/11 |
| 6,302,688 B1 | 10/2001 | Jordan et al. | |
| 6,582,226 B2 | 6/2003 | Jordan et al. | |
| 6,913,459 B2 * | 7/2005 | Fukutomi ....................... 433/8 |
| 2003/0064342 A1 | 4/2003 | Fukutomi | |
| 2003/0165790 A1 | 9/2003 | Castro et al. | |
| 2004/0086825 A1* | 5/2004 | Lai et al. ....................... 433/11 |

FOREIGN PATENT DOCUMENTS

| | | |
|---|---|---|
| EP | 0 727 192 | 8/1996 |
| WO | WO 2004/041109 | 5/2004 |

OTHER PUBLICATIONS

Design and Development of the Ultimate Ceramic Bracket, by D. Devanathan, designated "996-372E Apr. 2003" from TP Orthodontics, Inc.

* cited by examiner

*Primary Examiner*—Todd E. Manahan
(74) *Attorney, Agent, or Firm*—James D. Christoff

(57) ABSTRACT

An orthodontic appliance has a ceramic body and an archwire slot liner that is received in a channel of the body. The archwire slot liner has occlusal, gingival and lingual sections, and the lingual section is thicker than the occlusal or gingival section. The archwire slot liner helps resist fracture of the ceramic when the appliance is in use in the oral cavity, and yet need not adversely affect the aesthetic appearance of the appliance. A notch in the archwire slot liner is aligned with a channel in the body and provides a passageway for receiving a vertical auxiliary device.

21 Claims, 3 Drawing Sheets

CERAMIC ORTHODONTIC APPLIANCE WITH ARCHWIRE SLOT LINER

BACKGROUND OF THE INVENTION

1. Field of the Invention

This invention broadly relates to an appliance used in the course of orthodontic treatment. More particularly, the present invention relates to a ceramic orthodontic appliance having an archwire slot liner for receiving an archwire.

2. Description of the Related Art

Orthodontic treatment is directed to movement of the teeth to improved positions. Orthodontic treatment can greatly enhance the patient's facial appearance, especially in areas near the front of the patient's mouth. Orthodontic treatment can also improve the patient's occlusion so that the teeth function better with each other during mastication.

One type of orthodontic treatment involves the use of a set of appliances and archwires that are commonly known collectively as "braces". During treatment, tiny, slotted appliances known as brackets are affixed to the patient's anterior, cuspid and bicuspid teeth, and an archwire is placed in the slot of each bracket. The archwire forms a track to guide movement of the teeth to orthodontically correct positions. Ends of the archwire are often received in passages of small appliances known as buccal tubes that are affixed to the patient's molar teeth.

Orthodontic appliances are widely available in a variety of materials. Many orthodontists prefer to use appliances made of a metallic material such as stainless steel because metal appliances slide along metal archwires with relatively little resistance from the forces of friction. Unfortunately, metal appliances are often visible in the mouth and considered unaesthetic by many. The use of metal brackets sometimes leads to comments of a "metallic mouth appearance" that can be an embarrassment to the patient.

Some orthodontic appliances are made of a plastic material having a neutral color or a color that matches the color of the teeth. When new, plastic appliances are generally considered more aesthetic than metallic appliances. Unfortunately, some plastic appliances are stained by certain food and beverages and turn an unsightly color after a period of time. Moreover, the plastic material may slowly creep in use to such an extent that the archwire slot widens and precise control over movement of the tooth is rendered difficult.

Orthodontic appliances that are made of a transparent or translucent ceramic material overcome many of the problems associated with metal and plastic appliances. U.S. Pat. No. 4,954,080, assigned to the assignee of the present invention, describes a color-free ceramic bracket made of a polycrystalline material with a translucency that permits the natural color of the tooth to diffusely show through the bracket. Additionally, ceramic material is resistant to staining and does not deform by creep as in the case with plastic appliances.

Examples of orthodontic appliances made of a ceramic material are described in U.S. Pat. Nos. 5,358,402, 5,366,372, 5,380,196 and 5,439,379. The ceramic appliances that are described in those references have a metallic archwire slot liner that is located in a channel of the appliance. During treatment, the archwire is placed in the archwire slot liner and consequently a metal-to-metal contact between the archwire and the appliance is provided. Many practitioners prefer to use ceramic appliances with metallic archwire slot liners because they believe that the metal-to-metal contact between the appliances and the archwire provides better sliding mechanics than is typically observed with the use of ceramic appliances that lack metallic archwire slot liners.

Presently, there is a continuing interest in reducing the size of orthodontic appliances. Smaller appliances are more difficult to see in use and as a result are often considered more aesthetic. Although ceramic orthodontic appliances made of a translucent, colorless material are widely considered aesthetic, there is a continuing desire to reduce the size of such appliances to further enhance the patient's appearance during treatment.

Moreover, in some instances the appliances may come into contact with soft tissue, opposing dentition or other orthodontic appliances in the patient's oral cavity during the course of treatment. Such contact can lead to discomfort and occasionally pain that is best avoided if at all possible. Reducing the size of orthodontic appliances is a benefit, in that the probability of such contact is decreased.

Over the years, many attempts have been made to reduce the overall size of orthodontic appliances. Unfortunately, the reduction in appliance size may also reduce the fracture strength of the appliance to an amount that is deemed unacceptable. If an appliance fractures during the course of treatment, the patient should return to the practitioner for replacement of the appliance so that treatment can resume. As can be appreciated, appliance fracture represents a nuisance to both the practitioner and the patient in terms of time and expense.

SUMMARY OF THE INVENTION

The present invention is directed to a ceramic orthodontic appliance having an improved archwire slot liner that functions to increase the strength of the appliance. As a result, there is less likelihood that the appliance will fracture during use. The invention also enables the overall size of the appliance to be reduced so that it is less visible and hence considered more aesthetic to a casual observer during the course of treatment.

The ceramic orthodontic appliance of the present invention includes a lingual section, (i.e., a section facing in a direction toward the patient's tongue), an occlusal section (i.e., a section facing in a direction toward the outer tips of the patient's teeth) and a gingival section (i.e., a section facing in a direction toward the patient's gingival or gums). The archwire slot liner is received in a channel of a ceramic body of the appliance, and has a lingual wall section that tends to increase the strength of the appliance in regions of the ceramic body adjacent the lingual section.

In more detail, the present invention in one aspect relates to a ceramic orthodontic appliance that comprises a ceramic body having an elongated channel. The appliance also includes an archwire slot liner received in the channel. The liner includes an occlusal section having a certain thickness, a lingual section having a certain thickness and a gingival section having a certain thickness. The thickness of the lingual section is at least 250 percent of the thickness of at least one of the gingival section and the occlusal section, and each of the lingual, gingival and occlusal sections is bonded directly to the ceramic body.

Another aspect of the invention is directed to a method of making a ceramic orthodontic appliance. The method comprises:

providing a ceramic body having an elongated channel;

providing an archwire slot liner having an occlusal section, a lingual section and a gingival section, wherein the lingual section has a thickness that is greater than the thickness of at least one of the occlusal section and the gingival section;

placing the archwire slot liner in the channel of the ceramic body; and bonding each of the occlusal, lingual and gingival sections directly to the ceramic body.

In another aspect, the invention is directed to a combination of a ceramic orthodontic appliance and a vertical auxiliary device. The ceramic appliance includes a body having a first elongated channel extending in a generally mesial-distal direction and a second elongated channel extending in a generally occlusal-gingival direction. The appliance also includes an archwire slot liner received in the first channel, and the liner includes at least one notch aligned with the second channel to define a passageway. The vertical auxiliary device includes a portion that is received in the passageway. Advantageously, the present invention provides a ceramic appliance that has a strengthening archwire slot liner, and yet the archwire slot liner need not detract from the aesthetic appearance of the appliance. In ceramic brackets having archwire slot liners, the archwire typically covers the lingual section of the liner in use such that only the narrow, buccolabial edges (i.e., the edges facing the patient's lips or cheeks) of the occlusal and gingival sections can be observed. In the present invention, the thickness of the lingual section can be increased without adversely affecting the aesthetic qualities of the appliance since the lingual section is normally covered by the archwire during use. These and other aspects of the invention are described in more detail in the paragraphs that follow and are illustrated in the accompanying drawings.

DETAILED DESCRIPTION OF THE PREFERRED EMBODIMENTS

Figure 1:
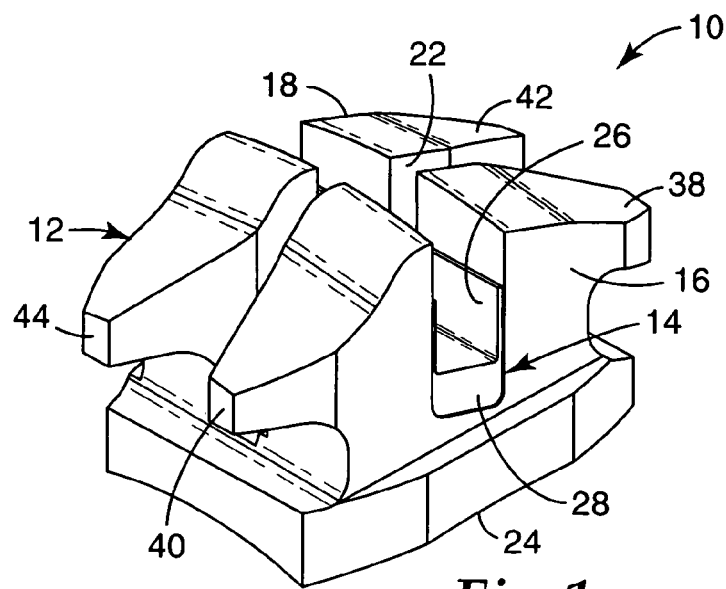
FIG. 1 is a perspective view of an orthodontic appliance constructed in accordance with one embodiment of the present invention, looking at the appliance toward its gingival, mesial and buccolabial sides.

An orthodontic appliance according to one embodiment of the invention is illustrated in FIGS. 1–2 and 4–6 and is broadly designated by the numeral 10. The appliance 10 includes a ceramic body 12 and an archwire slot liner 14 that is connected to the body 12. The archwire slot liner 14 is shown alone in FIG. 3.

The body 12 includes a mesial section 16 (i.e., a section facing toward the middle of the patient's dental arch) and a distal section 18 (i.e., a section facing away from the middle of the patient's dental arch). The mesial section 16 and the distal section 18 together present an elongated first channel 20 (FIG. 2) that receives the archwire slot liner 14. Preferably, but not necessarily, the archwire slot liner 14 and the channel 20 have identical lengths so that the archwire slot liner 14 extends from the mesial side of the mesial section 16 to the distal side of the distal section 18.

The body 12 has a second channel 22 that extends in a generally occlusal-gingival direction between the mesial section 16 and the distal section 18. Optionally, the second channel 22 serves as a debonding channel as explained below. Optionally, the second channel 22 has a depth in a lingual direction that is greater than the lingual direction of the first channel 20.

The body 12 also includes a base 24 for bonding the appliance 10 directly to the patient's tooth enamel by the use of an adhesive. Preferably, the base 24 has a contour that matches the contour of the patient's tooth surface to which it is bonded. For example, if the patient's tooth surface has a convex compound contour (i.e., has a convex shape when viewed in cross-sections along two mutually perpendicular reference planes), the base 24 preferably has a matching concave compound contour. Optionally, the base 24 is provided with grooves, particles, recesses, undercuts, a chemical bond enhancement material or any other material or structure or any combination of the foregoing that facilitates bonding the appliance 10 directly to the patient's tooth surface.

The archwire slot liner 14 has an occlusal section 26, a lingual section 28 and a gingival section 30. The occlusal section 26 and the gingival section 30 preferably extend in parallel reference planes, and the lingual section 28 preferably extends in a reference plane perpendicular to the sections 26, 30. The sections 26, 28, 30 together present an overall, generally "U"-shaped configuration when viewed in directions along the longitudinal axis of the archwire slot liner 14, as shown for example in FIG. 4. The sections 26, 28, 30 together define an archwire slot for receiving an archwire (not shown in the drawings).

In the illustrated embodiment, the inner sides of the sections 26, 28, 30 facing the archwire slot are generally flat, although other constructions are possible. For example, one or more of the sections 26, 28, 30 could be provided with protrusions, recesses, elongated grooves, ridges or other structure, such as may be desired for reducing the area of contact between the archwire slot liner 14 and the archwire. Examples of such structure are shown in U.S. Pat. Nos. 5,161,969 and 5,470,228, and U.S. Design Pat. No. 315,957, all of which are expressly incorporated by reference herein.

The lingual section 28 of the archwire slot liner 14 has a thickness that is at least 250 percent of the thickness (i.e., 2.5 times the thickness) of at least one of the occlusal section 26 and the gingival section 30. Preferably, the lingual section 28 has a thickness that is at least 250 percent of the thickness of each of the sections 26, 30. More preferably, the lingual section 28 has a thickness that is at least 400 percent of the thickness (i.e., four times the thickness) of each of the sections 26, 30. Optionally, the thickness of the occlusal section 26 is identical or substantially identical to the thickness of the gingival section 30. An example of a suitable construction is an archwire slot liner having a lingual section with a thickness of about 0.016 inch (0.4 mm), and having occlusal and gingival sections each with a thickness of about 0.004 inch (0.1 mm). As used in this paragraph, the "thickness" means the average thickness across the entire extent of the section.

Figure 2:
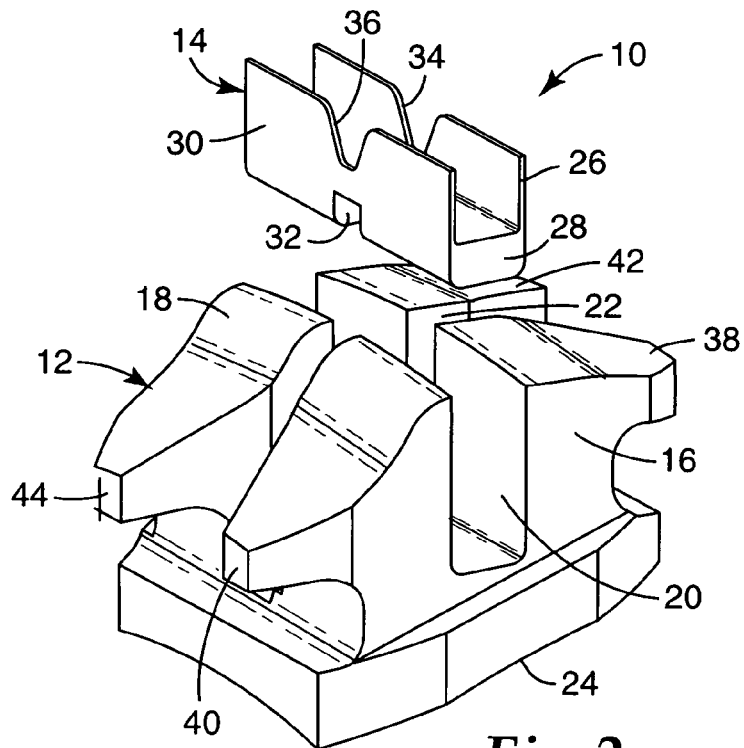
FIG. 2 is an illustration somewhat similar to FIG. 1, except showing the appliance in exploded view.
Figure 3:
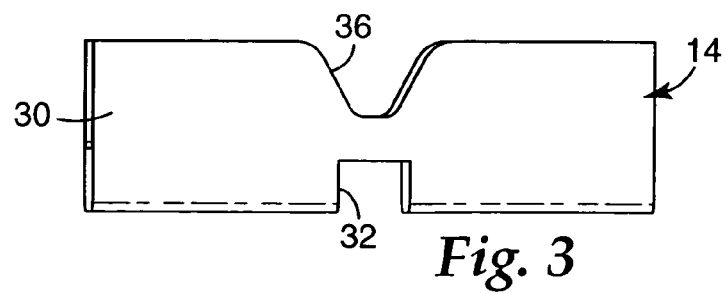
FIG. 3 is an enlarged side elevational view of an archwire slot liner alone of the appliance shown in FIGS. 1 and 2, looking in a direction toward a gingival section of the archwire slot liner.
Figure 4:
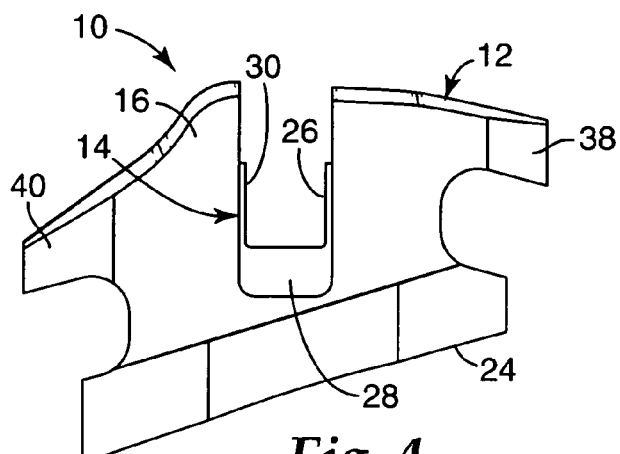
FIG. 4 is an end elevational view of the appliance shown in FIGS. 1 and 2, looking at the appliance in a direction toward its mesial side.

As illustrated in FIGS. 2 and 3, the lingual section 28 has a notch 32 that extends in a direction perpendicular to the longitudinal axis of the archwire slot liner 14. The notch 32 has an overall rectangular shape when viewed in directions along an occlusal-gingival reference axis, although other shapes are also possible. As shown for example in FIGS. 2 and 3, the notch 32 has an open lingual side.

The occlusal section 26 has a notch 34 that shown in FIG. 2. The gingival section 30 has a notch 36 that is shown in FIGS. 2 and 3. The notches 34, 36 have an overall, somewhat "V"-shaped configuration, although other shapes are also possible.

The notches 34, 36 are adjacent the notch 32. When the archwire slot liner 14 is assembled to the body 12, the notches 32, 34, 36 are aligned with the second channel 22. More specifically, a reference plane extending generally in an occlusal-gingival direction and bisecting the second channel 22 also bisects the notches 32, 34, 36. Preferably, the notch 32 and the second channel 22 together present a passageway 37 (see, e.g., FIG. 6) having a cross-sectional area adapted to slidably receive a portion of an orthodontic "vertical auxiliary" device such as an uprighting spring, pin or a hook. For example, a hook might be desirable in instances where the practitioner is seeking a means for connecting to one end of an elastic force module.

Figure 5:
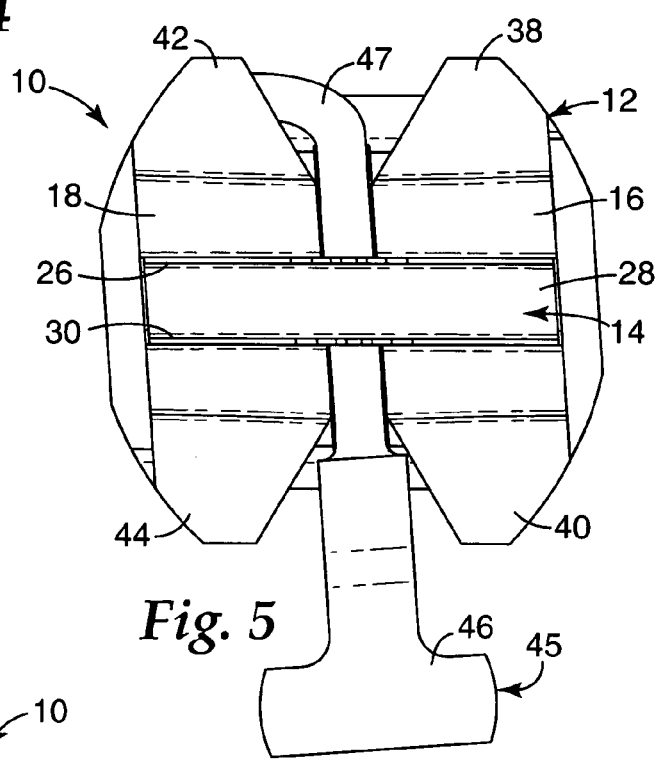
FIG. 5 is a front elevational view of the appliance shown in FIGS. 1, 2 and 4, looking at the appliance in a direction toward its buccolabial side, and also shows a vertical auxiliary device received in a passageway of the appliance.
Figure 6:
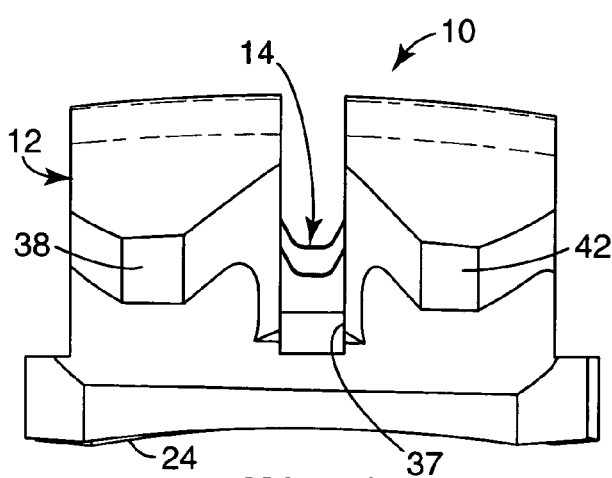
FIG. 6 is an end elevational view of the appliance shown in FIGS. 1, 2, 4 and 5, looking at the appliance in a direction toward its occlusal side.

In FIG. 5, the appliance 10 is illustrated in combination with a vertical auxiliary device known as a "T" hook 45. The hook 45 includes a stem 47 as well as a head 46 having a generally "T"-shaped configuration. The stem 47 is received in the passageway 37 and is located on the lingual side of an archwire when the archwire is received in the archwire slot liner 14. Preferably, the buccolabial face of the lingual section 28 extends over the passageway 37 and prevents contact of the archwire with the underlying portion of the stem 47 that is received in the passageway 37. Preferably, the stem 47 is bendable in order to securely connect the hook 45 to the appliance 10. As the stem 47 is bent, the outer end of the stem 47 may be conveniently positioned behind one of the tiewings such as tiewing 42 as shown in FIG. 5.

The second channel 22 facilitates removing the appliance 10 from the tooth at the conclusion of treatment. When the orthodontist desires to debond the appliance 10, a pliers-type tool is placed over the body such that one jaw of the tool engages the mesial side of the mesial section 16 and the other jaw of the tool engages the distal side of the distal section 18. Next, the handles of the tool are squeezed together in order to urge the jaws against the mesial and distal sides of the section 16, 18. As pressure is applied to the sections 16, 18 the body 12 fractures in a region along the lingual side of the channel 22, thereby enabling one or both of the sections 16, 18 to rock toward each other and detach from underlying areas of the tooth.

Additional aspects of the debonding procedure, along with further details and options for facilitating debonding are described in applicant's U.S. Pat. Nos. 5,366,372 and 5,439,379, both of which are expressly incorporated by reference herein.

In the embodiment depicted in FIGS. 1–6, the appliance 10 includes tiewings for ligating an archwire to the archwire slot of the archwire slot liner 14. In the exemplified embodiment, the mesial section 16 includes a mesial-occlusal tiewing 38 and a mesial-gingival tiewing 40. The distal section 18 includes a distal-occlusal tiewing 42 and a distal-gingival tiewing 44. In use, a ligature such as a tiny elastic O-ring or a section of wire is looped around the tiewings 38–44 as well as over the archwire in order to retain the archwire in the archwire slot.

Preferably, the archwire slot liner is made of a metallic material that provides sliding mechanics similar to the sliding mechanics observed with appliances that are entirely made of a metallic material. Suitable materials for the archwire slot liner 14 include stainless steel, such as series 300 or 17-4 PH stainless steel. Other materials may also be employed, such as titanium or gold, or materials having a stainless steel, titanium or gold coating. Additional examples of suitable materials (which may optionally be used as a coating over another material) include alloys of cobalt and chromium, alloys of iron, nickel and chromium and combinations thereof.

The archwire slot liner may be manufactured by any one of a number of techniques, and manufactured either separately from or together with the manufacture of the ceramic body. For example, the archwire slot liner 14 could be integrally made by a metal injection molding technique, by a machining process or by a casting process. Other techniques are described in applicant's U.S. Pat. Nos. 5,358,402 and 5,380,196, both of which are expressly incorporated by reference herein. The methods described in those references include methods where the liner is made in situ in the ceramic body.

In instances where the archwire slot liner 14 is manufactured separately from the body 12, any one of a number of methods may be subsequently used to couple the archwire slot liner 14 to the body 12. For instance, the archwire slot liner 14 may be connected to the body 12 by an adhesive, such as an epoxy or a dental or orthodontic adhesive. Other methods include a soldering process, a brazing process (such as the process described, for example, in the aforementioned U.S. Pat. Nos. 5,358,402 and 5,380,196) and a glazing technique (such as the use of a glass paste or slurry that is heated to its softening or melting temperature.

Preferably, the occlusal section 26, the lingual section 28 and the gingival section 30 are each directly bonded to the ceramic body 12. This construction enables the archwire slot liner 14 to enhance the strength of the appliance 10, particularly in areas of the body 12 that are adjacent the lingual section 28. This increase in strength is due to the increased thickness of the lingual section 28, as well as the bond between the sections 26, 28, 30 and the body 12. Ceramic materials typically exhibit high strength in compression but relatively low strength in tension. If, for example, the archwire slot liner 14 is made of a metallic material having a high tensile strength and is securely affixed to the ceramic material, the joined-together assembly is likely to present greater resistance to fracture than might be otherwise observed by use of a ceramic material alone.

Optionally, the archwire slot liner 14 is joined to the ceramic body 12 in such a manner that the ceramic body 12 is placed under compression. As a consequence, the relatively brittle ceramic body 12 is pre-stressed by the liner 14, such as is described in U.S. Pat. Nos. 5,380,196 and 5,439,379. As one option, the ceramic body 12 is pre-stressed by heating the ceramic body 12 and the archwire slot liner 14 as the archwire slot liner 14 is bonded to the body 12. Upon cooling, the greater thermal contraction of the archwire slot liner 14 relative to the body 12 enables the archwire slot liner 14 to thereafter retain the attached body 12 in compression. The difference in thermal contraction is due to the fact that the thermal expansion coefficient of the archwire slot liner 14 is greater than the thermal expansion coefficient of the ceramic body 12.

A variety of forces are typically encountered by orthodontic appliances during the course of treatment. For example, the archwire may exert a twisting force on the appliance in a rotative direction about the central, longitudinal axis of the archwire slot. When this type of force is exerted on the archwire slot liner 14, the lingual section 28 serves to resist relative movement of the occlusal tiewings 38, 42 and the gingival tiewings 40, 44 in directions away from each other so that the body 12 does not fracture.

As another example, the archwire may exert a pulling force on the appliance in an occlusal or gingival direction. For example, the patient may bite into a relatively hard food object that contacts the archwire in a location adjacent the appliance. In turn, the archwire may then exert a force on the gingival section 30 in a gingival direction. When this occurs, the lingual section 28 helps to resist undue stress on the gingival section 30 as well as adjacent areas of the occlusal tiewings 38, 42 so that the latter do not tend to fracture and break away from remaining portions of the body 12.

Advantageously, the overall size of the appliance 10 in directions along a buccolabial-lingual reference axis need not be increased. Instead, the channel 20 is deeper in a lingual direction than might be found, for example, in the corresponding channel of appliances known in the art. The decrease in ceramic material is replaced by the increased thickness of the lingual section 28, with the result that the fracture strength of the appliance is increased without a corresponding increase in the likelihood of patient discomfort or appliance fracture.

The ceramic body 12 may be made of any one of a number of materials, including monocrystalline as well as polycrystalline materials. Suitable monocrystalline materials include sapphire or single crystal aluminum oxide. Suitable polycrystalline materials include alumina-based ceramics such as described in U.S. Pat. No. 4,954,080 and Published U.S. Patent Application No. 2003-0165790.

Figure 7:
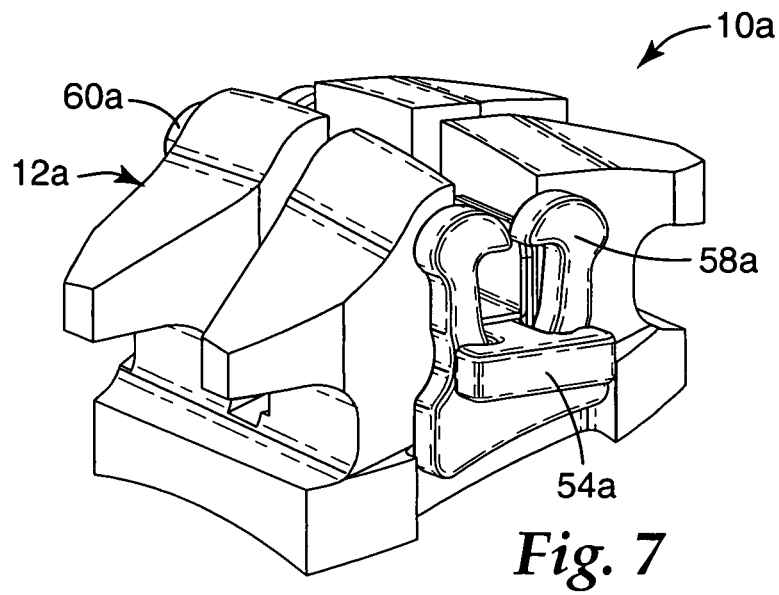
FIG. 7 is a perspective view of an orthodontic appliance according to another embodiment of the present invention, looking at the appliance toward its gingival, mesial and buccolabial sides.
Figure 8:
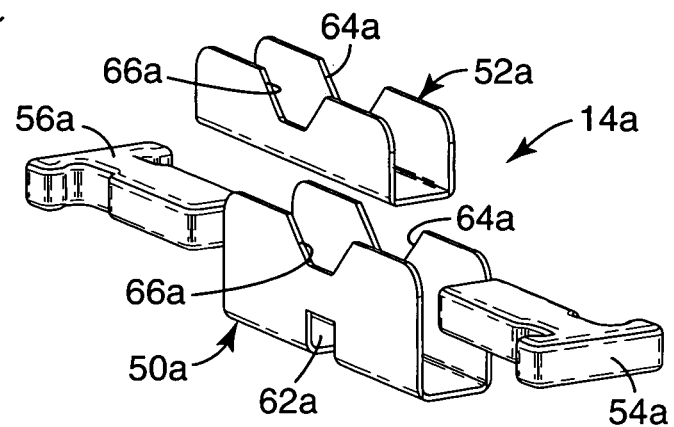
FIG. 8 is an illustration somewhat similar to FIG. 6 except showing the appliance in exploded view.
Figure 8:
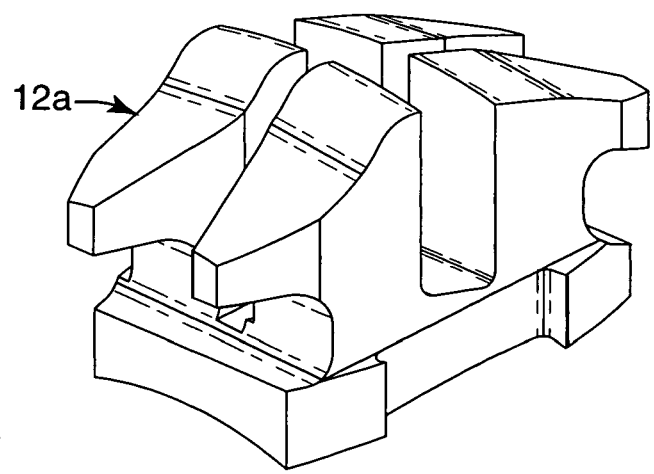

An orthodontic appliance 10a according to another embodiment of the invention is illustrated in FIGS. 7 and 8. The appliance 10a includes a ceramic body 12a and an archwire slot liner 14a. The body 12a is identical to the body 12 described above and as such a detailed description of the body need not be repeated.

The archwire slot liner 14a in the embodiment shown in FIGS. 7 and 8 comprises an assembly. The assembly includes an outer elongated member 50a having generally overall "U"-shaped configuration in longitudinally transverse cross-sectional view. The assembly also includes an inner elongated member 52a that also has a generally overall "U"-shaped configuration in longitudinally transverse cross-sectional view.

The archwire slot liner 14a also includes a mesial post 54a and a distal post 56a. Each of the posts 54a, 56a has a generally "T"-shaped configuration when viewed in directions along a buccolabial-lingual reference axis.

The post 54a, 56a provide support for an archwire latch of the appliance 10. In the illustrated embodiment, the latch comprises a mesial clip 58a and a distal clip 60a that are shown in FIG. 7 only.

Preferably, the clips 58a, 60a are constructed so that the archwire may be inserted into the archwire slot by pressing the archwire against the buccolabial side of the clips 58a, 60a. Additionally, the clips 58a, 60a preferably release the archwire from the archwire slot whenever the archwire exerts a force on the appliance 10a that exceeds a certain minimum value. The minimum value is significantly less than the force required in the same direction to debond the appliance 10a from the tooth, and consequently helps ensure that the appliance 10a will not spontaneously debond from the tooth during the course of treatment.

Additional details and aspects regarding the latch of the appliance 10a, including the clips 58a, 60a, are set out in U.S. Pat. Nos. 6,302,688 and 6,582,226, as well as in pending U.S. patent application Ser. No. 10/287,089 filed Nov. 4, 2002, all of which are expressly incorporated by reference herein.

When the archwire slot liner 14a is assembled, the inner member 52a is received in the outer member 50a, and the posts 54a, 56a are located in an area between a lingual section of the outer member 50a and a lingual section of the inner member 52a. The archwire slot liner assembly may be joined together by any suitable process such as by brazing, by welding or by use of an adhesive. As one example, the outer member 50a may be a braze foil that serves to bond the assembly to the body 12a.

Once the archwire slot liner 14a is placed in the body 12a, the posts 54a, 56a extend past the mesial and distal sections respectively of the body 12a. In the illustrated embodiment, the members 50a, 52a have equivalent overall lengths so that the posts 54a, 56a extend past the members 50a, 52a in a mesial and distal direction respectively, although other constructions are possible.

As shown in FIG. 8, the lingual section of the outer member 50a has a notch 62a that is similar to the notch 32 described above. In addition, the members 50a, 52a both include notches 64a, 66a located in occlusal and gingival sections respectively of the members 50a, 52a. The notches 62a, 64a, 66a are aligned with each other as well as with a second channel of the body 12a, similar to the position of the notches 32, 34, 36 with respect to the body 12 as set out above. Preferably, the lingual notch 62a and the second channel form a passageway having a cross-sectional area adapted to slidably receive a vertical auxiliary device such as is described above in connection with the embodiment shown in FIG. 5.

A number of other embodiments are also possible and will be apparent to those skilled in the art. Accordingly, the present invention should not be deemed limited to the specific examples that are exemplified above, but instead only by a fair scope of the claims that follow along with their equivalents.

The invention claimed is:

1. A ceramic orthodontic appliance comprising:

a ceramic body having an elongated channel; and an archwire slot liner received in the channel, wherein the liner includes an occlusal section having a certain thickness, a lingual section having a certain thickness and a gingival section having a certain thickness, wherein the thickness of the lingual section is at least 250 percent of the thickness of at least one of the gingival section and the occlusal section, wherein each of the occlusal section, the lingual section and the gingival section is bonded directly to the ceramic body, wherein the liner is an assembly that comprises an outer elongated member having a generally overall "U"-shaped configuration in longitudinally transverse cross-sectional view, and wherein the assembly also includes an inner elongated member that is received in the outer member.

2. A ceramic orthodontic appliance according to claim 1 wherein the thickness of the lingual section is at least 250 percent of the thickness of each of the gingival section and the occlusal section.

3. ceramic orthodontic appliance according to claim 1 wherein the thickness of the lingual section is at least 400 percent of the thickness of at least one of the occlusal section and the gingival section.

4. A ceramic orthodontic appliance according to claim 1 wherein the liner is coupled to the body by an adhesive.

5. A ceramic orthodontic appliance according to claim 1 wherein the liner is connected to the body by a braze material.

6. A ceramic orthodontic appliance according to claim 1 wherein the liner is connected to the body by a glaze material.

7. A ceramic orthodontic appliance according to claim 1 wherein the inner member has a generally overall "U"-shaped configuration.

8. A ceramic orthodontic appliance according to claim 1 wherein the outer member includes a lingual wall having a central notch.

9. A ceramic orthodontic appliance according to claim 1 wherein the assembly also includes at least one post located between the outer member and the inner member, and wherein the post extends outwardly past the ceramic body.

10. ceramic orthodontic appliance according to claim 9 wherein the appliance includes at least one latch extending about the post for connecting an archwire to the appliance.

11. A ceramic orthodontic appliance according to claim 10 wherein the latch comprises a self-releasing clip.

12. A ceramic orthodontic appliance according to claim 1 wherein the appliance is a bracket.

13. A ceramic orthodontic appliance according to claim 1 wherein the body has a mesial section, a distal section and an elongated channel extending generally in an occlusal-gingival direction between the mesial section and the distal section, and wherein the liner includes at least one notch aligned with the channel.

14. A ceramic orthodontic appliance according to claim 13 wherein at least one notch is located on the lingual section of the liner.

15. A ceramic orthodontic appliance according to claim 13 wherein at least one notch is located on at least one of the gingival section and the occlusal section of the liner.

16. A ceramic orthodontic appliance according to claim 13 wherein the liner includes three notches, and wherein each notch is located on a corresponding one of the gingival section, the occlusal section and the lingual section.

17. ceramic orthodontic appliance according to claim 1 wherein the thickness of the occlusal section is approximately equal to the thickness of the gingival section.

18. An orthodontic appliance including a ceramic body having a first elongated channel extending in a generally mesial-distal direction and a second elongated channel extending in a generally occlusal-gingival direction, the appliance also including an archwire slot liner received in the first channel, wherein the liner includes an occlusal section having a certain thickness, a gingival section having a certain thickness and a lingual section having a thickness that is greater than the thickness of the occlusal section and the gingival section, wherein the lingual section of the liner includes at least one notch aligned with the second channel to define a passageway and wherein the at least one notch has an open lingual side.

19. An orthodontic appliance according to claim 18 wherein the liner includes a lingual section, and wherein at least one notch is located on the lingual section.

20. An orthodontic appliance according to claim 19 wherein the liner includes a gingival section and an occlusal section that also include at least one notch.

21. An orthodontic appliance according to claim 18 wherein the body has a mesial section and a distal section, wherein the second channel extends between the mesial section and the distal section, and wherein the mesial section and the distal section can be squeezed together toward the second channel in order to enable the appliance to be debonded from a tooth.

* * * * *

UNITED STATES PATENT AND TRADEMARK OFFICE
CERTIFICATE OF CORRECTION

PATENT NO. : 7,192,274 B2 Page 1 of 1
APPLICATION NO. : 10/730344
DATED : March 20, 2007
INVENTOR(S) : Allen J. Stadtmiller It is certified that error appears in the above-identified patent and that said Letters Patent is hereby corrected as shown below:

Column 9
Line 5, In Claim 3, before "ceramic" insert -- A --.
Line 27, In Claim 10, before "ceramic" insert -- A --.

Column 10
Line 9, In Claim 17, before "ceramic" insert -- A --.

Signed and Sealed this

Fifth Day of June, 2007

JON W. DUDAS
*Director of the United States Patent and Trademark Office*